United States Patent [19]

Hagihara

[11] 4,311,151
[45] Jan. 19, 1982

[54] OXYGEN MEASURING ELECTRODE ASSEMBLY

[76] Inventor: Bunji Hagihara, 8-17, Fujishirodai 2-chome, Suita, 565, Japan

[21] Appl. No.: 85,397

[22] Filed: Oct. 16, 1979

Related U.S. Application Data

[63] Continuation-in-part of Ser. No. 932,217, Aug. 9, 1978, abandoned.

[30] Foreign Application Priority Data

Aug. 24, 1977 [JP] Japan .................................. 52-101235
Oct. 22, 1977 [JP] Japan .................................. 52-126988

[51] Int. Cl.³ .............................................. A61B 5/00
[52] U.S. Cl. .................. 128/635; 204/195 B; 204/195 P
[58] Field of Search ........................ 128/635, 632; 204/195 B, 195 P

[56] References Cited

U.S. PATENT DOCUMENTS

| | | | |
|---|---|---|---|
| 3,659,586 | 5/1972 | Johns et al. ........................ | 128/635 |
| 3,795,239 | 3/1974 | Eberhard et al. ................... | 128/635 |
| 3,918,434 | 11/1975 | Lubbers et al. ..................... | 128/635 |
| 3,933,593 | 1/1976 | Sternberg ............................ | 128/635 |
| 3,985,633 | 10/1976 | Lubbers et al. ..................... | 128/635 |
| 3,998,212 | 12/1976 | Reichenberger .................... | 128/635 |
| 4,185,620 | 1/1980 | Hagihara ............................. | 128/635 |

OTHER PUBLICATIONS

Evans et al., "The Systemetic O₂ Supply . . . ", Resp. Phys., 1967, 3, pp. 21–37.

Primary Examiner—Lee S. Cohen
Attorney, Agent, or Firm—Cushman, Darby & Cushman

[57] ABSTRACT

A polarographic electrode assembly for transcutaneous measurement of partial oxygen pressure in arterial blood comprising an anode, a cathode which has a thin ring surface or a circularly-bounded field of dot-shaped surfaces and an insulating electrode holder, a disposable tubular member holder fixedly holding the periphery of an oxygen permeable hydrophobic electrode membrane, and a skin-heating part including heat-conducting block which is thermally connected to a heater and a temperature detector. The heat-conducting block has a thick peripheral portion and thin disk-shaped inner portion having a through-hole to expose the cathode surface to the subject's skin via the membrane. One side of the heat-conducting block has a smooth surface to be applied on skin, and the back side has a receiving space for the membrane holder. The heat-conducting block embraces the membrane holder which embraces the anode and cathode portion of the electrode part in such a manner that the membrane covers the working surfaces of the anode and cathode via an electrolyte layer. In a prefabrication step the membrane is strongly bonded in a uniformly stretched condition to the holder for stability of sensitivity of the electrode. By using such a cathode a good correlation coefficient of measured $PO_2$ over actual arterial $PO_2$ and a good S/N ratio are provided, and by using a skin heating block having a sufficient heating area a highly stable electrode sensitivity is assured.

12 Claims, 11 Drawing Figures

OXYGEN MEASURING ELECTRODE ASSEMBLY

REFERENCE TO RELATED APPLICATION

This is a continuation-in-part of my copending application, Ser. No. 932,217, filed Aug. 9, 1978, abandoned in favor hereof.

BACKGROUND OF THE INVENTION

This invention relates to a polarographic electrode assembly suitable for transcutaneous measurement of partial oxygen pressure in arterial blood. A measurement of a partial oxygen pressure in arterial blood is an important matter in breath control of a new-born baby or a patient in intensive care.

Hitherto, for measuring the concentration of oxygen, namely the oxygen partial pressure $PO_2$, in blood, the method most generally used has been that of measuring oxygen in the blood extracted from an artery. But, the method is not suitable for continuous measurements, and moreover, the method has the problem of being painful for the patient. Especially for a new-born baby, breath control is necessary in order to prevent an impediment of its brain due to low oxygen concentration while preventing damage in its retina due to excessive oxygen concentration. For such new-born baby, the oxygen concentration in the atmosphere surrounding the baby must be carefully controlled by using the measured value of oxygen partial pressure in arterial blood, and for that purpose a continuous or real-time measurement of oxygen partial pressure is necessary. A method of retaining an oxygen electrode in an artery for the continuous measurement can be considered, but this method requires a high handling skill and is likely to invite a great danger. Therefore, such a method has not been widely used.

The transcutaneous oxygen electrode method, being different from the direct measurement method, does not give the patient any pain. The method is suitable for long continuous measurement, since it catches oxygen at the skin surface and measures the oxygen which diffuses from the blood and through the skin. The transcutaneous oxygen electrode is essentially a kind of Clark-type electrode, but the former has a constant temperature-heating means to warm the patient's skin for arterialization. When it is attached on the patient's skin, oxygen diffusing from the arterialized subcutaneous tissue reaches the surface of a cathode of noble metal through an electrode membrane disposed between the skin and the electrodes. Then the oxygen reacts with the cathode and is reduced to water. By measuring the electrolytic current produced by this electrode reduction, the oxygen partial pressure $PO_2$ can be obtained. In such measurement, by heating the part of the skin that contacts the electrode to a suitable temperature, the subcutaneous tissue is locally arterialized, thereby making the oxygen partial pressure to be measured practically equal to that of the arterial blood.

There are two representative known types of transcutaneous arterial blood oxygen measuring electrode assemblies, but these known ones have respective shortcomings and hence are inconvenient in handling. Especially, stable fixing of the electrode members is very difficult and their measured values are not sufficiently stable.

One of these types is the anode heating type which has a very fine needle cathode supported coaxially in a thick tubular anode which is heated at a constant temperature of 43°–44° C. Heating of the skin for local arterialization is carried out by this anode with an insulating material filled therein.

The construction of the anode heating type electrode assembly is elucidated referring to FIG. 1. As shown in FIG. 1, a few fine platinum wires 1 of about 0.015 mm diameter for cathodes are disposed in an insulating glass cylinder 3, and a cylindrical anode 2 of silver is disposed to surround the glass cylinder 3. And an oxygen-permeable membrane 4 of 12 μm Teflon (trademark), PTFE is attached on one end face of the anode 2 and cathodes 1 and fixed by an O-ring 9 on a side face of an electrode holder 7 of plastics. A heater 5 is disposed around the anode 2 so as to heat the anode 2 to a constant temperature by the aid of a temperature detecting unit 6 in the glass cylinder 3. A collar 8 of plastics fixed to the electrode holder 7 has a contact face which is to be secured by double-side adhesive tape 12 to the skin 13 of a patient. A small amount of an electrolyte 11 is retained in a thin space between the end faces of the electrodes and the membrane, and another amount of the electrolyte is in a reservoir space 10 which is connected to the thin space. Also, a small amount of contact liquid 14 is filled between the membrane 4 and the skin 13.

The abovementioned anode heating type electrode assembly has the following problems. Due to the very small area of the working surfaces of the cathodes, it gives a good correlation coefficient of the measured value over actual arterial value, but by the same reason it has poor signal to noise ratio (S/N ratio). Secondly, since the plane membrane 4 is fixed by O-ring 9 on the side face of the cylindrical electrode holder 7, the membrane face is likely to have wrinkles and membrane stretch is not uniform and stable. Therefore, a uniform contact of the membrane 4 with the working surfaces of cathodes 1, which is necessary for stable measurement, cannot be fully expected. Thirdly in order to obtain partial oxygen pressure of the arterial blood by heat-arterialization of the subcutaneous tissue, this type of electrode assembly heats the skin by silver anode through the electrolyte layer and the electrode membrane, and the heating condition is not very stable.

The principle of the transcutaneous measurement of the partial oxygen pressure by using the anode heating type electrode assembly is elucidated referring to FIG. 1. Then the electrode assembly is stuck on the skin 13 of a patient by the double-face adhesive tape 12 at the end face of plastic collar 8 and the anode 2 is heated to 43°–44° C., the skin tissue at the part under the anode 2 and its neighboring skin tissue are heated thereby arterializing the skin tissue. Therefore, the partial oxygen pressure in the blood vessel in the heated skin tissue become substantially equal to that in the arterial blood. The oxygen diffuses from the blood vessel through the skin tissue, passes the membrane 4, dissolves in the electrolyte 11 consisting mainly of KCl solution and reaches the surface of the cathode 1. When a specified D.C. potential of 0.5 to 0.8 volts is applied across the cathode and the anode in a manner that the anode is positive to the cathode, by reaching of oxygen to the electrode surface, a reduction reaction of the oxygen takes place at the cathode surface, and an oxidation reaction of the silver takes place at the anode. Namely, on the surface of the cathode of gold or platinum, the reduction reaction is, in case that the electrolyte is acidic:

$$O_2 + 4H^+ + 4e \rightarrow 4H_2O \ldots \quad (1),$$

or, in case that the electrolyte is basic:

$$O_2 + 2H_2O + 4e \rightarrow 4OH^- \ldots \quad (2).$$

In both of the above reactions, electrons of a number proportional to the amount of the $O_2$ molecules reaching the cathode are consumed.

At the same time, on the surface of the anode 2 of silver, the oxidation reaction is, for any value of pH:

$$4Ag + 4Cl^- \rightarrow 4AgCl - 4e \ldots \quad (3),$$

thus electrons of the number corresponding to the amount of the $O_2$ reaching the cathode are produced. Accordingly, a current flows between the anode and the cathode, and the intensity of the current is proportional to the number of oxygen molecules which pass through the membrane and hence is proportional to the partial oxygen pressure in the subcutaneous tissue and to the arterial blood.

A second known transcutaneous oxygen electrode assembly is a cathode heating type having a disk shaped working surface of cathode disposed coaxially in a tubular anode. One of this type of the prior art is shown in FIG. 2. A cathode of the electrode assembly consists of a platinum cylinder 1' of a large diameter having a backing copper block 1'', and heater winding 5 is located in an encircling recess which is provided around the copper block 1'' so as to directly heat the cathode 1. An anode 2 consists of silver ring coaxially disposed around the cathode 1 with an insulator or electrode holder 7 in between. An electrode membrane 4 is a thin film of plastics (e.g. Teflon) disposed on the end faces of the cathode 1 and the anode 2 with electrolyte 11 in between, and the membrane 4 is secured by a substantially annular plastic collar 8. An actual electrode assembly of the cathode heating type has the construction as shown in FIG. 2(b), wherein cathode 1 has such a large diameter as 3 mm, and the membrane 4 is 6 μm thick polyester film held by inserting and pinching at its periphery between the annular capsule 8 and the cylindrical electrode holder 7.

The electrode assemblies of FIG. 2(a) and FIG. 2(b) have the following problems. Firstly, although a large area for cathode is selected, this area is not enough for the purpose of heating the skin, because the cathode is disposed in the anode whose size is limited for stable membrane fitting. In addition to this the skin is heated by this cathode via the electrolyte layer and membrane, and hence the heating of the skin tends to be insufficient. Secondly, since the cathode has a large area, the amount of the electrolytic reaction and hence the consumption of the electrolyte held becomes large, and this causes a large drift of the electrode sensitivity and a short lifetime for the electrode. Thirdly, since the cathode surface has a large round area, the distances to the anode and hence the exchange of the electrolytes are not equal in the central part and in the peripheral part. Therefore, the overall current of the cathode reaction does not precisely respond to the change in the partial oxygen pressure. Fourthly, since the large working surface of the cathode consumes a large amount of oxygen, the oxygen flux in the skin tissue becomes large. This causes the skin to disturb the flow of oxygen, and hence the partial oxygen pressure is measured as a smaller value than in actually is, in the other words, a poor correlation coefficient of the measured value over the true value is obtained. Such measurement error can be reduced to some extent by using an electrode membrane of relatively low oxygen permeability, for example, 6 micron thick polyester film. However, use of such a membrane results in a slow response in measurement.

Fifthly, since the electrode membrane 4 is secured by pinching the peripheral part by inserting it between the electrode holder 7 and the collar 8, the membrane is likely to have wrinkles, and tension on the membrane is not stable, thereby resulting in unstable sensitivity of the electrode.

In both of the conventional devices of FIGS. 1(a), 1(b) and FIGS. 2(a), 2(b) stretching tension of the membrane is not strong due to the loose fixing methods, and in addition to this, a wide range of the membrane area is exposed to skin. Accordingly, even a small change in the contacting condition of the electrode membrane to the skin is likely to make a change of the thickness of the electrolyte layer and hence changing the electrode sensitivity and making the measurement unstable.

SUMMARY OF THE INVENTION

The present invention purposes to provide an improved electrode assembly for accurate transcutaneous partial oxygen pressure measurement, whereby the above-mentioned drawbacks are eliminated. Special features of the present electrode assembly are as follows: 1. Differing from the conventional way of membrane holding, the present assembly adopts a prefabrication technique which includes strongly bonding a membrane on a holder. In an assembled state, uniform and sufficiently strong stretching of the membrane is reproducibly obtained. Therefore, the electrode sensitivity is significantly stabilized due to the establishment of a stable gap containing an electrolyte layer between the membrane and the cathodes. 2. By using a cathode having a thin ring shaped surface or a plurality of dot shaped surfaces disposed on or in a circle, small working surface(s) are distributed in a wide area, and therefore, the electrode assembly gives a good correlation coefficient of the measured $PO_2$ to true arterial $PO_2$, while keeping good S/N ratio. 3. Instead of heating the skin for arterialization by using the anode or cathode, the present assembly adopts a special skin heating block of a suitable heating area having a small hole for exposing the cathode via the membrane. Therefore, heating of the skin is carried out more directly and stably than in the conventional methods where the skin is heated via the electrolyte layer and the membrane. This heating method contributes also to eliminating instability of the electrode sensitivity that is liable to accompany the prior art electrode heating methods.

DETAILED DESCRIPTION OF THE INVENTION

Figure 1A:
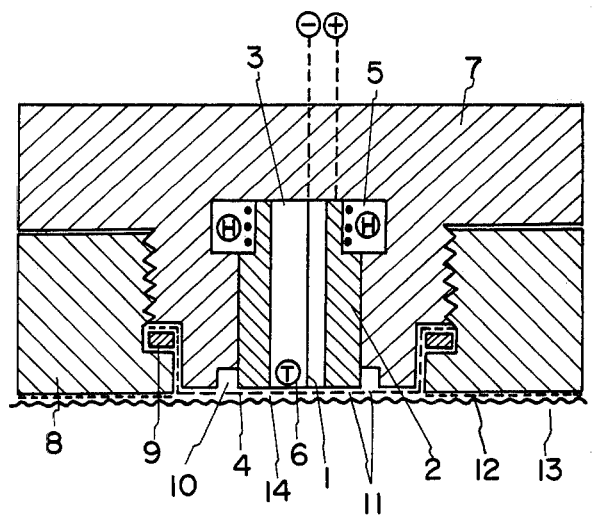
FIG. 1(a) is a sectional elevation view of a first conventional electrode assembly.
Figure 1B:
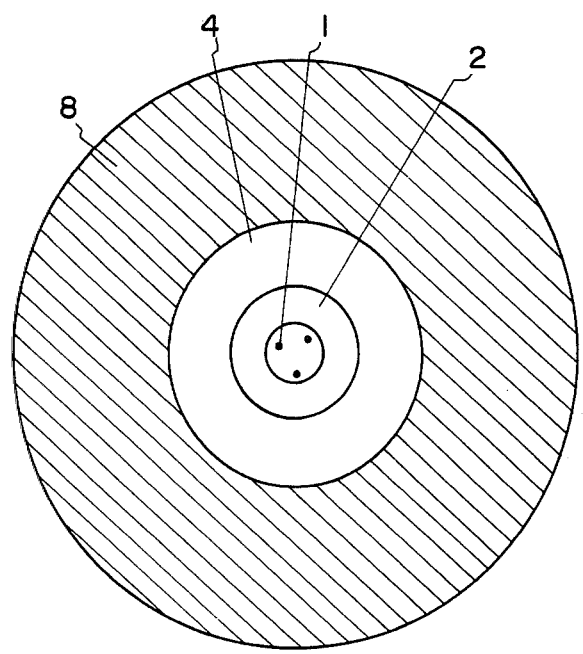
FIG. 1(b) is a bottom view of the electrode assembly of FIG. 1(a).
Figure 2A:
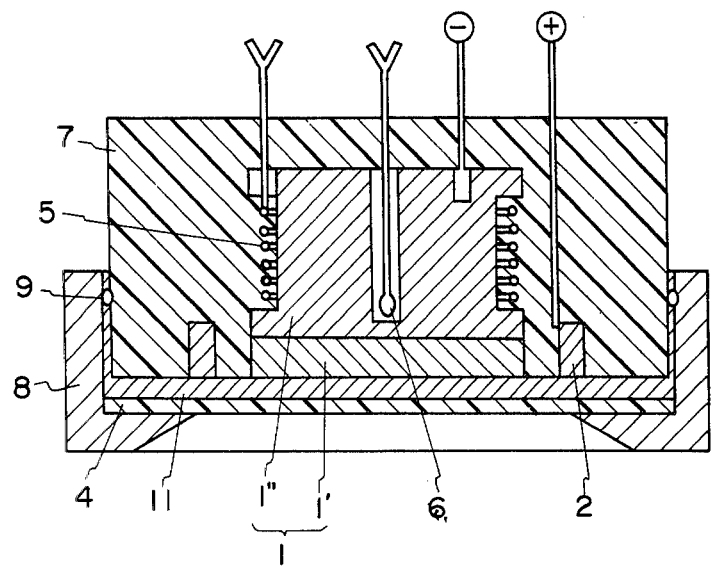
FIG. 2(a) is a sectional elevation view of a second conventional electrode assembly.
Figure 2B:
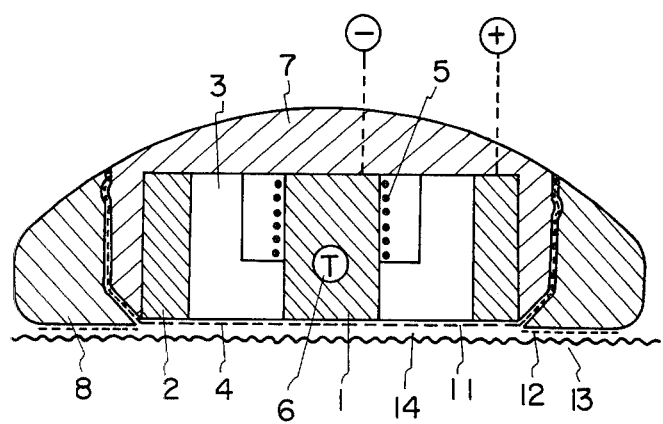
FIG. 2(b) is a sectional elevation view of an actual electrode assembly made by utilizing the design of FIG. 2(a).

The polarographic electrode assembly for transcutaneous measurement of partial oxygen pressure according to the present invention is characterized by the following novel construction.

The assembly comprises three fundamental parts, namely, an electrode part, a disposable membraneholder part and a skin-heating part.

The electrode part comprises a cathode means of small working surface(s) spreading over a wide area, an anode disposed to encircle the cathode, an insulator to hold the cathode in a spaced relation to the anode and an electrode holder 7 which holds the anode and also serves as a lid for the whole electrode assembly.

The disposable membrane-holder part comprises an electrode membrane to be attached when assembled to the working surface of the cathode and anode, and a membrane holder to which the electrode membrane is fixedly held.

The skin-heating part comprises a heat-conducting metal block shaped to embrace the membrane-holder part and the electrode part. An electric heater and a temperature detecting unit are disposed in a good heat conductive relation to the thick collar portion of the heat-conducting block. The inner portion of the heat-conducting block is provided in the shape of a thin disk and has an opening at the center for exposing a specified part of the electrode membrane therethrough.

The abovementioned electrode part, membrane-holder part and skin-heating part are assembled together in a manner such that the membrane-holder part is put in the skin-heating part, and the electrode part is put on the heating part like a lid so that the electrodes portion of the electrode part is substantially inserted in an inside space of the membrane holder, thereby to form a rigid electrode assembly.

In the electrode part, the cathode of the present invention is characterized by having a very small total area of exposed working surface, which area is spread over a relatively wide range. Preferably, the cathode face is provided in the shape of a very fine ring or in an array of very small dots disposed on a circle. Also, the dot-shaped surfaces may be evenly arranged in a circular area. Being shaped in such ways, the total area of the working face surface of the cathode can be made desirably small. Empirically it is found that the cathode can react only with the oxygen molecules passing through the area within the range specified by a distance from a point immediately under the cathode. For example, provided that the layer of electrolyte is sufficiently thin and the thickness of the electrode membrane is about 20 $\mu$m, then an oxygen-passing area, namely the area of skin, from which oxygen molecules come to the cathode face, should the area be within about 100 $\mu$m from the cathode. The ratio S/C, which is the ratio of oxygen-passing area of skin S to the working surface area C of the cathode, becomes large as the cathode surface becomes small. On the other hand, the rate of oxygen consumption by the cathode is almost proportional to the cathode surface area. Accordingly, when the ratio S/C is large, necessary oxygen-flux in the skin becomes small. For example, a cathode of 0.03 mm diameter has an oxygen-flux of only one-fiftieth of that of a 2 mm diameter cathode. When the oxygen-flux is sufficiently small, there is practically no restriction for passing of oxygen through the skin. In such case, the oxygen transport barrier of the skin (epidermis) practically disappears, and the partial oxygen pressure value measured on the skin closely approaches the actual value in the arterialized subskin tissue (dermis) whose oxygen partial pressure is equilibrated with that of the arterial blood. When the S/C ratio is sufficiently large due to small working surface of cathode, there is no need to use a special membrane of low $O_2$-permeability, and therefore, the response of the measurement is greatly improved by the use of a highly oxygen-permeable membrane.

Although a very small working surface of the cathode gives a high S/C ratio and hence a good correlation coefficient of measured/actual value, this working surface produces only a small oxygen reduction current. In order to remove this drawback, the working surface(s) of the cathode of the present electrode assembly is shaped as either a very thin ring or a large number of small dots arranged on or in a circle disposed coaxially with the face of the anode. Such small and spread-out surface(s) of the cathode gives high S/C ratio as in the case of a single small surface, but the output signal of the former and hence its signal to noise ratio is much larger than the latter case, since the total working surface is increased.

The membrane-holder part of the present invention is entirely a new device. It is constructed by fixing the periphery of the electrode membrane on the annular end face of the membrane holder. A preferred way of fixing is bonding by an adhesive. By prefabricating a subassembly comprising the membrane bonded on the holder in a mass-production line, a uniform tension and smooth surface of the membrane are obtainable, thereby assuring an accurate gap with, and unform contact force to, the working surface of the cathode.

The skin-heating part comprises a heat path includng a heater, a heat detecting element and a block of heat conductive material with a smooth skin-contacting surface, all connected in a good heat-conductive manner. The heat path is substantially separated from the cathode and anode, unlike heating through the anode or cathode as in the abovementioned prior art devices. 3y providing the heat block separately from the anode or cathode, a desirably large heat capacity is obtainable, thereby improving accuracy of temperature control. By utilizing a large skin-contacting surface on the heat conducting block, a sufficiently wide area of the skin is uniformly heated thereby enabling sufficient arterialization of the subcutaneous tissue. Although the skin-contacting surface has an opening for passing oxygen, by selecting the opening as small as possible, uniformity and accuracy of the temperature of the skin in the area to be tested are secured. Due to the strong blood flow along the skin, an opening of less than 4 mm diameter has no interfering effect on heating the part of skin facing the opening.

When the skin-contacting thin metal sheet is additionally stuck on the abovementioned skin-heating face of the heat conducting block and the skin-contacting sheet has an opening still smaller than that in the heat conducting block, this sheet is very effective to protect the electrode membrane from the pressure of the skin. In the assembled state, the cathode is exposed via the membrane through this small opening and the sheet masks the membrane around the opening. In this way, pressing of the skin toward the membrane is largely prevented, because the part of the membrane to be pressed by the skin is limited to the small exposed area. Therefore, the thickness of the electrolyte layer in the gap between the membrane and the electrode surface becomes stable as designed, thereby stabilizing the sensitivity of the electrode assembly, and hence reliability of the measurement.

By shaping the insulator which holds the cathode to the anode in such a manner that the end face of the insulator to contact th electrode membrane has a smooth shoulder part and on the other hand, the skin-contacting sheet and a part of the heat-conducting block form a ring-shaped corner to correspond with the shoulder part, the electrode membrane is protruded by the cathode insulator and thus a desirable tension is given to the electrode membrane.

Figure 3:
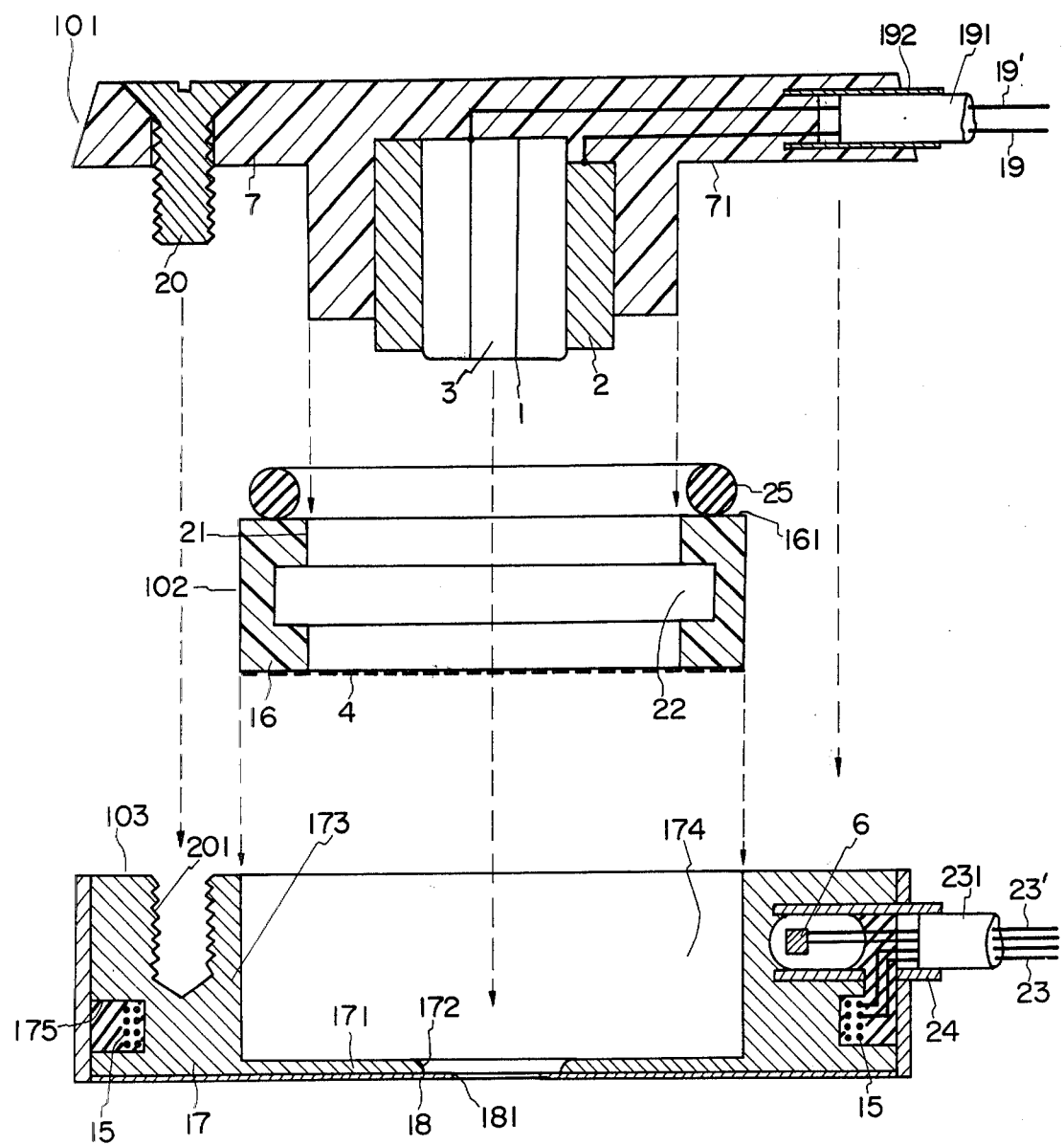
FIG. 3 is an exploded sectional elevation view of an electrode assembly of the present invention.
Figure 4:
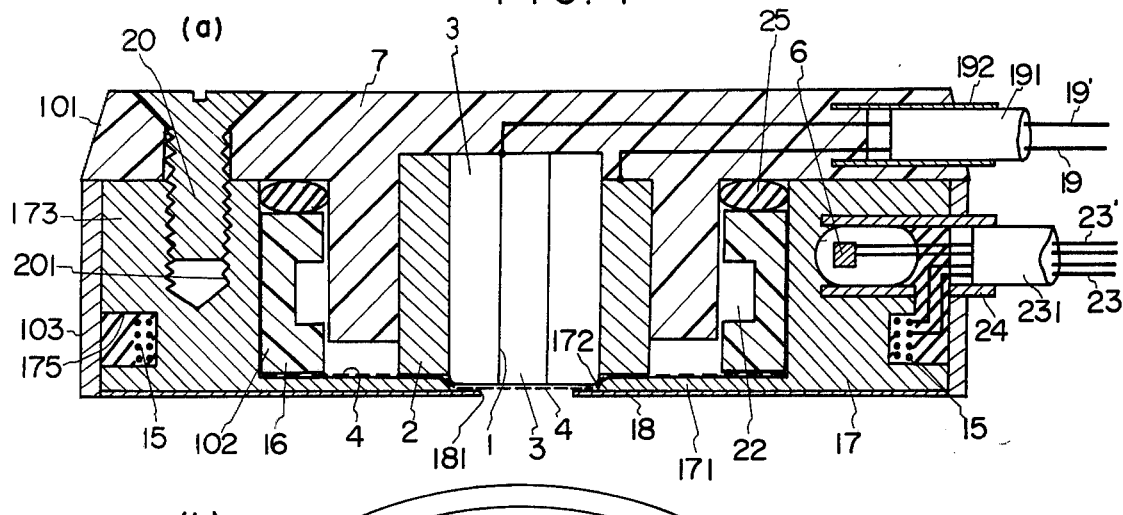
FIG. 4 is an assembled sectional elevation view of the electrode assembly of the present invention of FIG. 3.
Figure 4:
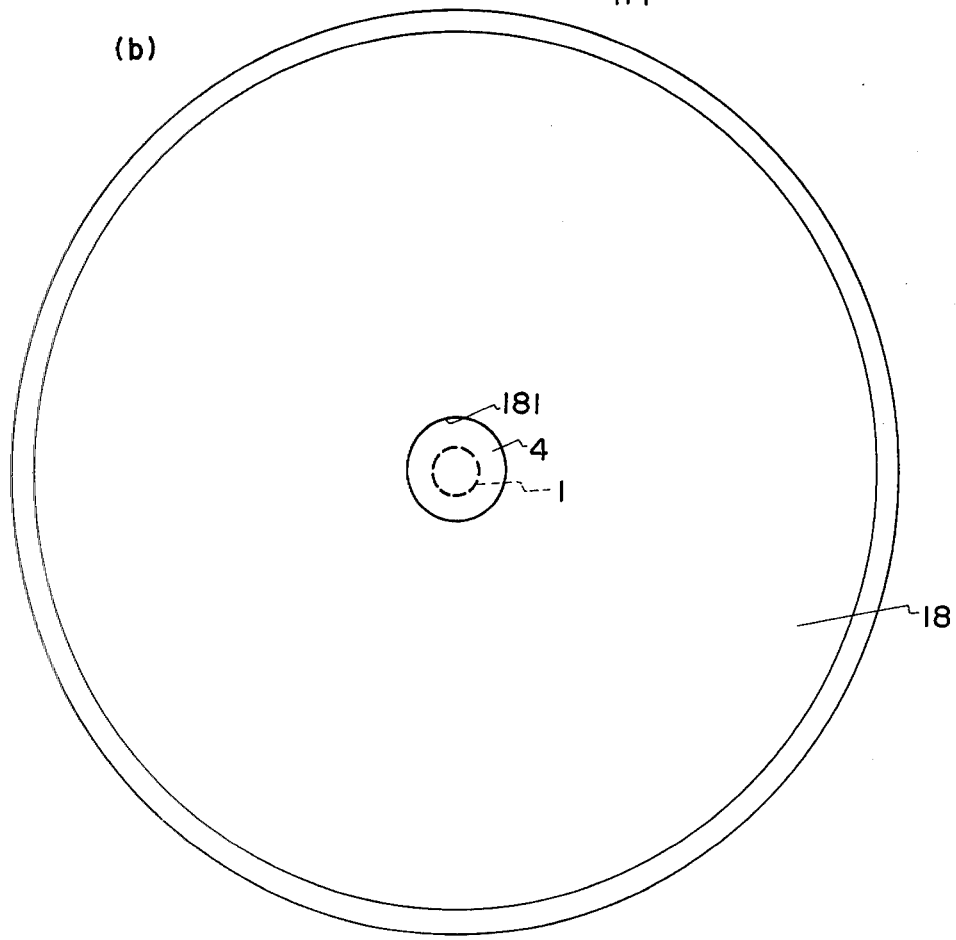

A preferred example embodying the present invention is elucidated referring to FIG. 3 showing an exploded sectional elevation view and FIG. 4 showing an assembled sectional elevation view.

For convenience in description, the axially downward direction in FIGS. 3 and 4 is referred to as the axially inner direction, while the opposite direction is referred to as the axially outer direction. Geometrical terms used have their usual meaning as understood from the context and drawings. As shown in FIG. 3, the oxygen measuring electrode assembly of the present invention comprises an electrode part 101, a membrane-holder part 102 and a skin-heating part 103.

The electrode part 101 comprises an electrode holder 7 made of insulting material, for example engineering resin such as fluorine-containing resin or polycarbonate resin. The electrode holder holds a cathode and an anode and also constitutes a lid part 71 of the electrode assembly. The cathode 1 of the example of FIG. 3 and FIG. 4 is a thin cylindrical tube of platinum or gold, coaxially disposed inside a thick cylindrical tubular anode 2 of silver and is held by an insulator 3 of glass or epoxy resin filled in between. The space inside the tubular cathode 1 is filled with the insulator of glass or resin. The cathode 1 and the anode 2 are connected to lead-out wires 19' and 19, respectively. In this embodiment, the outer diameter of the cathode at its axially inner end coincides with an imaginary circumscribing circle within which lies the axially inner end surface of this cathode.

Figure 8:
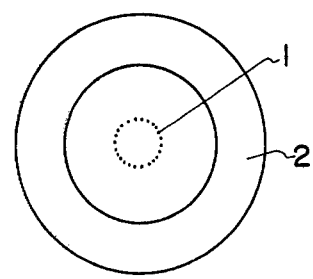
FIG. 8 is a bottom view of an arrangement of an anode and cathodes of a modified example of the present invention.
Figure 9:
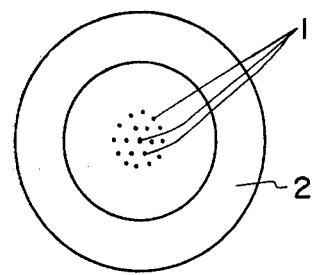
FIG. 9 is a bottom view of an arrangement of an anode and cathodes of a modified example of the present invention.

As shown in modified examples of cathode arrangements in FIG. 8 and FIG. 9, the cathode can be constituted with many fine wires. One end of each wire is connected to a lead-out wire 19' in FIG. 3 and the other end is disposed on or inside an imaginary circumscribing circle which is coaxial to the surface of the anode facing the membrane. In this way the single cathode has a plurality of dot-shaped working surfaces spread in a limited area, that being the area lying within said imaginary circumscribing circle. The reason that the cathode is shaped as a thin cylindrical tube or as a plurality of fine wires of circular disposition is for the purpose of achieving a high correlation coefficient of the measured $PO_2$ over the true arterial value for the aforementioned reason.

The abovementioned anode 2 and cathode 1, which are firmly secured to each other by the insulator 3, are molded in the electrode holder 7, thereby constructing the electrode part 101. The surface of the anode 2 is preferably disposed axially a little behind the surfaces of the cathode 1 and the insulator 3, in order to give a tension to the electrode membrane 4 when the latter is attached to the surfaces of the electrodes. The electrode holder 7 has a fastening means, such as screws 20 for connecting it to the skin-heating part 103 when assembled. Lead-out wires 19 and 19' for the cathode 1 and the anode 2 are sheathed in an insulating cord 191, which is fixed through a guard tube 192 to the electrode holder 7.

The membrane-holder part 102 comprises a cylindrical tubular membrane-holder 16 made of insulating material such as the engineering resin and an electrode membrane 4 of plastic film. The membrane holder has a ring-shaped cavity 22 in an inside space thereof. The ring-shaped cavity 22 serves as a reservoir and ballast for electrolyte solution and air in a space inside the membrane. A ring-shaped packing of an elastic material, such as O-ring 25 is disposed between the upper face 161 of the membrane holder 16 and the lower face 71 of the lid part of the electrode holder 7, so as to push the electrode holder toward the inner disk-shaped portion 171 of the heat conducting block 103, and at the same time, seal the space containing the electrolyte from the ambient atmosphere.

The electrode membrane 4 should be an oxygen-permeable, hydrophobic film which is not permeable for water and electrolytes. Such film can be at least one of polyvinylidenechloride, polytetrafluorethylene, polypropylene and polyester. Generally speaking, if the working surface of the cathode is large and oxygen consumption by the electrode reaction is excessively large, a membrane having a low oxygen permeability has to be used to compensate for the effect of the excessive oxygen-consumption. Such use of a low oxygen permeable membrane results in a slow response. However, in the device of the present invention, since the working area of the cathode is sufficiently small, a membrane having a considerably high oxygen permeability can be used, and hence, a quick response is achieved, while keeping a good correlation coefficient of the measured value to the true value.

In the actual example, for the electrode membrane 4, a 15–30 $\mu m$ thick film of polytetrafluoroethylene, a 10–20 $\mu m$ film of tetrafluorethylene-trifluoropolypropylene copolymer, a 10–20 $\mu m$ polypropylene, film or a 5–10 $\mu m$ polyvinylidene chloride film is preferable.

The polytetrafluoroethylene film is superior in having a low hygroscopicity, but, is extremely water-repellent. Accordingly, this membrane has poor wetting property with the electrolyte, and is likely to reduce the stability of the electrode assembly. As a result of many empirical tests, the present inventor has found that the hygropscopicity of a polytetrafluoroethylene membrane can be much improved by etching one side of the membrane by corona discharge or treating it with an ammonium solution of metallic sodium, thereby stabilizing the electrode reaction. The abovementioned or similar treatments are also effective for other kinds of membranes. Firm bonding of the membrane 4 to the membrane-holder 16 is made by thermoplastic bonding for thermoplastic films or by heated adhesive bonding using a hot-melt type adhesive for other films through a pre-treatment. When utilizing such prefabrication of the membrane part 102 with the electrode membrane 4 fixed to the membrane holder 16, wrinkles undesirable scattering of tension, which have hitherto occurred as a result of individual bonding of the membrane by unskilled users, can be eliminated, thereby assuring stable and reliable measurement.

The reservoir space 22 in the membrane holder 16 serves to reserve electrolyte and air. Accordingly, when the electrolyte in the gap between the membrane 4 and the electrodes is consumed or exhausted, the electrolyte or the necessary component thereof is fed from the reservoir, thereby assuring a long-time continuous measurement.

The heating part 103 shown in FIG. 3 comprises a block 17 of a metal having good heat conductivity such as copper or aluminum alloys and a skin-contacting sheet 18 of thin resilient metal such as stainless steel or phosphor bronze.

The heat-conducting block 17 comprises a thick radially outer peripheral part 173 and a relatively thin, disk-shaped radially inner part 171 extended from the lower part of the peripheral part 173. The peripheral part 173 has a threaded hole 201 for receiving the or each screw 20 for securing the electrode part 101 on the heating part, and also has a ring-shaped groove 175 in which a heater 15 is disposed. The heater 15 is preferably comprised of a heater wire such as a manganin or Cu-Ni alloy wire. A temperature-detecting element 6 such as a thermister for detecting the temperature of the metal block 17 is disposed therein. Lead-out wires 23 and 23' for the heater 15 and the temperature detecting element 6, respectively are sheathed in an insulating cord 231, which is fixed through a guarding tube 24 of stainless steel or the like material to the metal block 17. Preferably, the peripheral part 173 and the disk-shaped inner part 171 are formed as one unit in order to achieve good heat conduction, and form a receiving space 174 in which the membrane part 102 and the electrodes of the electrode part 101 are received. The heat-conducting block 17 has a considerable heat capacity and hence serves to stabilize the temperature thereof. The disk-shaped inner part 171 of the block has a through-hole 172, the diameter of which is a little larger than the diameter of the lower face of the insulator 3.

The skin-contacting sheet 18, which is, for example, a stainless steel plate of a thickness of about 0.05 mm, is heat-conductively connected by welding, soldering or by a suitable adhesive to the lower face of the disk-shaped inner part 171. The skin-contacting plate 18 has a through-hole or an opening 181 of a size smaller than the through-hole 172 of heat-conducting block 17 but a little larger than the ring, or the circle, of the cathode disposition, at the center part for exposing the cathode surface(s) via the electrode membrane 4 therethrough. A desirable example of the diameter of the hole 181 is about 2.5 mm.

The electrode part 101, the membrane-holder part 102 and the skin-heating part 103 are assembled together by putting the membrane-holder part 102 into the receiving space 174 of the heating part 103 and further putting the electrode part 101 on the heating part 103 and the membrane part 102. Before the assembling step is conducted, a specified small amount of electrolyte is put on the center part of the inner side of the electrode membrane 4. Then part of the electrolyte is held between the membrane 4 and the lower end face of the cathode 1 and the insulator 3 and the rest is retained in the reservoir space 22.

By fastening with the screws 20 (in the actual device, three screws), the above three parts of the electrode assembly are fixed together as shown in FIG. 4. The electrode assembly is fixed to the skin by attaching the skin-contacting sheet 18 to the skin by means of, for example, a ring-shaped piece of two-side adhesive film disposed in between, with a drop of water as a contact liquid put between the electrode membrane 4 exposed through the opening 181 of the skin contacting sheet 18 and the skin.

In general, the electrode membrane should be disposed as near as possible to the skin surface. In a case where the membrane is disposed very close to the skin, the membrane is likely to be excessively pressed by the skin surface, thereby changing the thickness of the electrolyte layer and hence the measured valve. However, by disposing the skin-contacting plate 18 of thin but strong metal sheet with its small hole 181 in front of the membrane, excessive pressure on the membrane is avoided. And furthermore, by pressing the part of the periphery of small hole 181 of the skin-contacting sheet 18 in an air-tight relation to the membrane 4, and by infiltration of a part of the contacting liquid laterally into the gap between the skin-contacting plate 18 and the electrode membrane 4, the adverse effect of oxygen straying into the gap and resultant lowering of the response speed can be eliminated.

Figure 5:
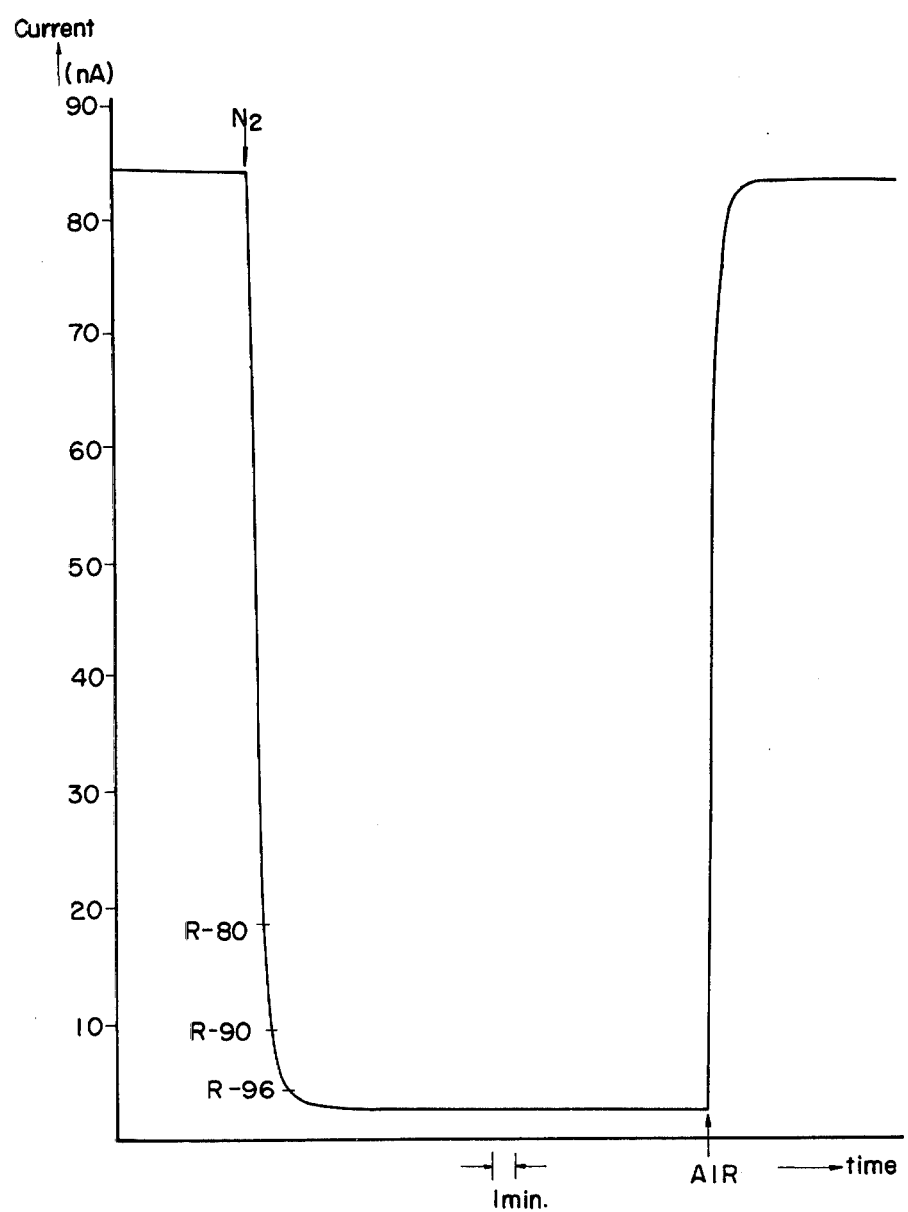
FIG. 5 is a graph showing a calibration curve of the electrode assembly having the construction as shown in FIG. 4.
Figure 6:
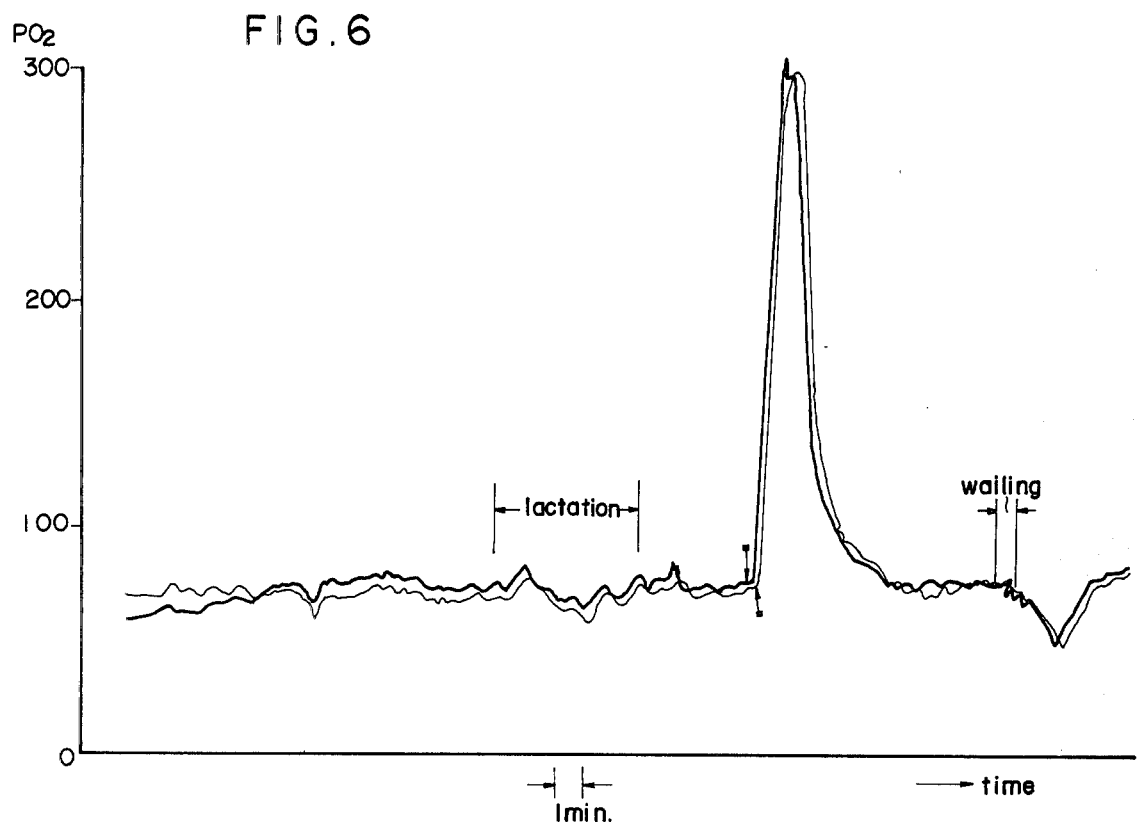
FIG. 6 is a graph showing response curves of the partial oxygen pressure in the arterial blood of a newborn baby measured by the electrode assemblies of the present invention.
Figure 7:
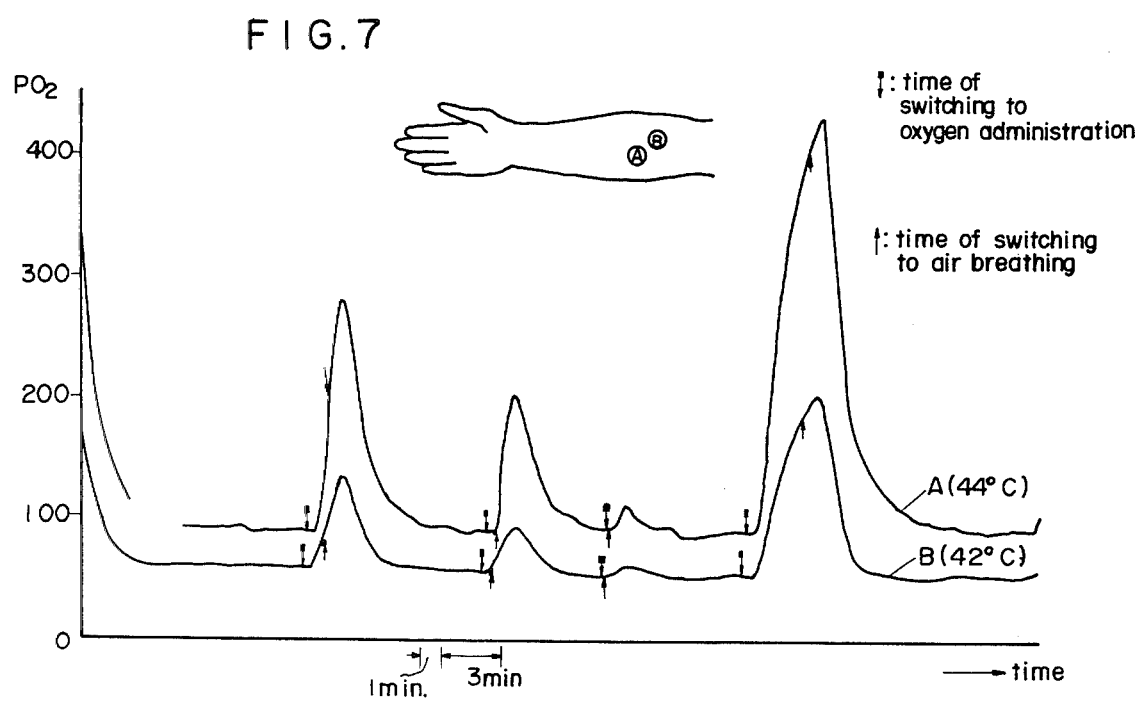
FIG. 7 is another graph showing response curves of the partial oxygen pressure in the arterial blood of an adult measured by the electrode assemblies of the present invention.

FIGS. 5, 6 and 7 are charts showing examples of the curves obtained by continuous recording of the signals from the electrode assembly embodying the present invention.

FIG. 5 is a calibration curve showing the electrolysis current obtained with two gases of known $PO_2$ values, namely dry air and nitrogen. Details of the construction of the electrode assembly used here are:

| | |
|---|---|
| diameter of the skin-contacting sheet 18 | 18mm |
| thickness of the skin-contacting sheet 18 | 0.05mm |
| diameter of the through-hole 181 | 2.5mm |
| shape and material of the anode | thick silver tube |
| inner diameter of the anode 2 | 3.0mm |
| outer diameter of the anode 2 | 5.0mm |
| shape and material of the cathode | platinum thin tube |
| diameter of the cathode | 1.0mm |
| thickness of the cathode | 0.02mm |
| electrolyte | aqueous solution of 1M KCl, 0.1 M ethanolamine buffer pH 10 and 50% glycerol. |
| electrode membrane | 50μm thick tetrafluoroethylene film, the inner side of which is etched by sodium treatment. |

D.C. Voltage applied between the cathode and the anode is 0.7 volt and the temperature of the heat-conducting block is 44° C.

Before the calibration, a D.C. voltage of 0.7 volt is applied between the anode and the cathode by using a known stabilized D.C. source with a known current measuring means together, and the temperature of the heat-conducting block is set at 44° C. by using a known temperature regulating circuit. The electrode assembly is then mounted on a calibrating port of a calibration chamber, and calibrating gases of dry air and nitrogen are sent alternatively to the port so as to contact the electrode membrane. When the dry air having the $PO_2$ value of 160 mm Hg is sent and the currrent is recorded, the stationary value of 84.5 nA was obtained as shown in FIG. 5. When the air at the calibration port is then replaced by nitrogen having the $PO_2$ value of 0, the current rapidly decreases almost to zero, and becomes stable at a specified small stationary value of about 1.5 nA. When the air is again sent to the calibration port in place of the nitrogen, the current increases rapidly at first and then gradually to reach the stationary value of 84.5 nA in due course.

Experiments show that 80% response time is about 20 seconds, 90% response time is about 30 seconds and 96% response time is about 50 seconds.

FIG. 6 is a graph showing the time courses of the change in the arterial partial oxygen pressure of a newborn baby measured by the aforementioned electrode assemblies of the present invention. In this case a 20 $\mu$m polypropylene film is used as the electrode membrane and two sets of the electrode assemblies are fixed on an upper part and a lower part of the right breast. The curves are recorded by using a dual-pen recorder which records the measured currents to show partial oxygen pressures. As shown in the graph, the partial oxygen pressure rapidly rises upon the administration of oxygen, which is shown by two arrows on the curves, then falls upon returning after one minute to air-breathing, and then comes back to the original level after a specified time period. It is observed that even during the air-breathing, the partial oxygen pressure is always changing. For example, it slightly falls at lactation, and further, greatly falls at wailing. Through comparison of the values of the transcutaneous measurement by the abovementioned electrode with the values of partial oxygen pressure actually measured in the collected arterial blood, it is observed that the correlation coefficient of the transcutaneously measured value to true arterial value is about 0.95.

FIG. 7 is a graph showing the time courses of change in the partial oxygen pressures of an adult transcutaneously measured at different temperatures. Two electrode assemblies A and B, whose temperatures are set at 44° and 42° C., respectively, are fixed on the skin of an inside forearm of a 30 year old man as shown in the sketch in the graph. Each of the electrode assemblies is made embodying the present invention and has an electrode membrane of 12 $\mu$m polyvinylidene chloride. When air-breathing and oxygen administration are alternately made, the curves A and B are obtained by the electrode assemblies A and B, respectively. The arrows on the curves indicate the time when the oxygen and air are switched from each other. The graph shows the fact that the measurement by the electrode assembly set at 44° C. reflects the changes of partial oxygen pressure in the arterial blood much more faithfully than that at 42° C. It was observed that the correlation coefficient of the measured transcutaneous value to the arterial value is about 0.8 and 0.5 at 44° and 42° C., respectively.

What is claimed is:

1. A polarographic electrode assembly for transcutaneous measurement of partial oxygen pressure in arterial blood, comprising:

(a) an electrode part, including as an electrode unit:
   an anode having a ring-shaped working surface;
   cathode means constituting a cathode having working surface means constituting a working surface disposed within an imaginary circumscribing circle and perimetrically surrounded by said ring-shaped working surface of said anode, with radial spacing between said anode working surface and said cathode working surface means; and
   an electrode holder of insulative material, said electrode holder holding said anode and said cathode means, maintaining said radial spacing, and providing an electrically and thermally insulated relationship for said anode and said cathode means relative to one another;

(b) a membrane holder part, including:
   an oxygen-permeable hydrophobic electrode membrane having an outer peripheral margin; and
   a cylindrical tubular membrane holder having an axially inner annular end face and an axially outer annular end face with a longitudinal bore extending between them;
   means fixedly circumferentially holding said outer peripheral margin of said electrode membrane on said axially inner end face of said cylindrical tubular membrane holder with a predetermined, circumferentially substantially uniform tension and with said electrode membrane extending across said longitudinal bore; and (c) a skin heating part, including:
   an integral, heating conducting metal block having a radially inner relatively thin disk-shaped portion and a radially outer, relatively thick annular peripheral portion, each of these portions having an axially outer side and an axially inner side, the two axially inner sides being substantially axially aligned so as to provide one substantially flat surface incorporating both of them, but the axially outer side of said relatively thin disk-shaped portion lying substantially axially inwardly of said axially outer side of said relatively thick annular peripheral portion, so as to provide an electrolyte well having said axially outer side of said relatively thin disk-shaped portion as its bottom and a radially inwardly facing generally cylindrical surface of said relatively thick annular peripheral portion as its sidewall;
   means providing a generally central hole axially through said relatively thin disk-shaped portion of said integral, heat conducting block, said through hole communicating with said well and being of a size and shape large enough to expose therethrough substantially all of said working surface means of said cathode means when said electrode unit is telescopically axially received in said well;
   said substantially flat surface being adapted to be presented in confronting relation to the skin of a subject who is to be monitored, said substantially flat surface being larger in area than said through hole; and
   an electric heater and a temperature-detecting element, both being mounted on said skin heating part so as to form a unitary subassembly therewith;
   said electrode unit being axially telescopically removably received in the bore of said membrane holder part and both said electrode unit and said membrane holder part being axially telescopically removably received in said well of said skin heating part, with both said anode working surface and said cathode working surface means closely confronting said electrode membrane; said electrode membrane extending across said through hole to provide a portion thereof axially exposed through said through hole and having said cathode working surface means in operable relationship therewith.

2. A polarographic electrode assembly in accordance with claim 1, wherein:
said working surface of said anode is a larger ring and said working surface means of said cathode means is a smaller ring disposed in a coaxial relation with said working surface of said anode.

3. A polarographic electrode assembly in accordance with claim 1 wherein:
said working surface means of said cathode means is constituted by a plurality of dot-shaped working surfaces uniformly disposed in a ring-shaped array which is in a coaxial relation with said working surface of said anode.

4. A polarographic electrode assembly in accordance with claim 1, wherein:
said working surface means of said cathode means is constituted by a plurality of dot-shaped working surfaces uniformly disposed within an imaginary circle which is in a coaxial relation with said working surface of said anode.

5. A polarographic electrode assembly in accordance with claim 1, wherein:
said working surface means of the cathode means protruding from a plane on which said periphery of said electrode membrane lies, thereby in assembled state said electrode membrane being set with a predetermined tension.

6. A polarographic electrode assembly in accordance with any one of claims 1, 2, 3, 4 and 5 wherein said working surface means of said cathode means is made of a noble metal selected from a group consisting of platinum and gold.

7. A polarographic electrode assembly in accordance with claim 1, wherein:
said skin heating part further includes a skin-contacting metal sheet which is thinner than said thin disk-shaped inner portion of said heat-conducting metal block but has an axial face which is larger in area than said circumscribing circle, said skin contacting metal sheet being heat-conductingly fixed on said substantially flat surface so as to perimetrically mask the radially outer margin of said portion of said electrode membrane that is exposed through said through hole of said disk shaped inner portion while exposing a limited region of said electrode membrane which is surrounded by said masked margin, and said working surface means of said cathode means being disposed on said limited region of said electrode membrane.

8. A polarographic electrode assembly in accordance with claim 7, wherein:
said working surface of said anode is a larger ring and said working surface means of said cathode means is a smaller ring and said working surface of said anode and said working surface means of said cathode means are disposed in a coaxial relation with each other.

9. A polarographic electrode assembly in accordance with claim 7, wherein:
said working surface means of said cathode means is constituted by a plurality of dot-shaped working surfaces uniformly disposed in a ring-shaped array which is in a coaxial relation with said working surface of said anode.

10. A polarographic electrode assembly in accordance with claim 7, wherein:
said working surface means of said cathode means is constituted by a plurality of dot-shaped working surfaces uniformly disposed within an imaginary circle which is in a coaxial relation with said working surface of said anode.

11. A polarographic electrode assembly in accordance with claim 7, wherein:
said working surface means of the cathode means protruding from a plane on which said periphery of said electrode membrane lies, thereby in assembled state said electrode membrane being set with a predetermined tension.

12. A polarographic electrode assembly in accordance with any one of claims 7 to 11 wherein working surface means of said cathode means is made of a noble metal selected from a group consisting of platinum and gold.

* * * * *